(12) United States Patent
Tran et al.

(10) Patent No.: US 8,771,344 B2
(45) Date of Patent: Jul. 8, 2014

(54) TRANSCATHETER HEART VALVE DELIVERY SYSTEM WITH REDUCED AREA MOMENT OF INERTIA

(71) Applicants: Don Tran, Novato, CA (US); Nathan Wiemeyer, Healdsburg, CA (US); Susheel Deshmukh, Santa Rosa, CA (US); Leonel Mendoza, Rohnert Park, CA (US); Matthew Rust, Santa Clara, CA (US)

(72) Inventors: Don Tran, Novato, CA (US); Nathan Wiemeyer, Healdsburg, CA (US); Susheel Deshmukh, Santa Rosa, CA (US); Leonel Mendoza, Rohnert Park, CA (US); Matthew Rust, Santa Clara, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/967,894

(22) Filed: Aug. 15, 2013

(65) Prior Publication Data
US 2014/0005769 A1    Jan. 2, 2014

Related U.S. Application Data

(62) Division of application No. 12/757,111, filed on Apr. 9, 2010, now Pat. No. 8,512,400.

(51) Int. Cl.
*A61F 2/24*    (2006.01)

(52) U.S. Cl.
USPC ....................................... 623/2.11

(58) Field of Classification Search
CPC . A61F 2002/9534; A61F 2/2436; A61F 2/95; A61F 2002/9522; A61F 2002/9528; A61F 2/2427; A61F 2/966; A61F 2002/9665; A61M 2025/0004; A61B 2017/22035; A61B 17/3468

USPC ......... 606/108, 191, 194, 198, 200; 623/1.11, 623/1.23, 2.1, 2.11, 2.12
See application file for complete search history.

(56) References Cited

U.S. PATENT DOCUMENTS

| 5,628,755 | A | 5/1997 | Heller et al. |
| 5,683,451 | A | 11/1997 | Lenker et al. |
| 5,824,041 | A | 10/1998 | Lenker et al. |
| 5,906,619 | A | 5/1999 | Olson et al. |
| 5,957,949 | A | 9/1999 | Leonhardt et al. |

(Continued)

FOREIGN PATENT DOCUMENTS

| FR | 2932376 | 12/2009 |
| GB | 2433700 | 7/2007 |

(Continued)

*Primary Examiner* — Ryan Severson
*Assistant Examiner* — Katherine M Shi

(57) ABSTRACT

A device for percutaneously repairing a heart valve of a patient including a self-expanding, stented prosthetic heart valve and a delivery system. The delivery system includes delivery sheath slidably receiving an inner shaft forming a coupling structure. A capsule of the delivery sheath includes a distal segment and a proximal segment. An outer diameter of the distal segment is greater than that of the proximal segment. An area moment of inertia of the distal segment can be greater than an area moment of inertia of the proximal segment. Regardless, an axial length of the distal segment is less than the axial length of the prosthesis. In a loaded state, the prosthesis engages the coupling structure and is compressively retained within the capsule. The capsule is unlikely to kink when traversing the patient's vasculature, such as when tracking around the aortic arch, promoting recapturing of the prosthesis.

11 Claims, 10 Drawing Sheets

(56) References Cited

U.S. PATENT DOCUMENTS

| | | |
|---|---|---|
| 2003/0040736 A1 | 2/2003 | Stevens et al. |
| 2003/0199963 A1 | 10/2003 | Tower et al. |
| 2004/0147939 A1 | 7/2004 | Rabkin et al. |
| 2005/0137688 A1 | 6/2005 | Salahieh et al. |
| 2006/0004439 A1 | 1/2006 | Spenser et al. |
| 2006/0052867 A1 | 3/2006 | Revuelta et al. |
| 2006/0259136 A1 | 11/2006 | Nguyen et al. |
| 2006/0265056 A1 | 11/2006 | Nguyen et al. |
| 2007/0005131 A1 | 1/2007 | Taylor |
| 2007/0088431 A1 | 4/2007 | Bourang et al. |
| 2007/0239266 A1 | 10/2007 | Birdsall |
| 2007/0239269 A1 | 10/2007 | Dolan et al. |
| 2007/0270932 A1 | 11/2007 | Headley et al. |
| 2008/0065011 A1 | 3/2008 | Marchand et al. |
| 2008/0082165 A1 | 4/2008 | Wilson et al. |
| 2008/0147160 A1 | 6/2008 | Ghione et al. |
| 2008/0147181 A1 | 6/2008 | Ghione et al. |
| 2008/0188928 A1 | 8/2008 | Salahieh et al. |
| 2009/0048668 A1 | 2/2009 | Wilson et al. |
| 2009/0093876 A1 | 4/2009 | Nitzan et al. |
| 2009/0138079 A1 | 5/2009 | Tuval et al. |
| 2009/0171447 A1 | 7/2009 | von Segesser et al. |
| 2009/0171456 A1 * | 7/2009 | Kveen et al. ............... 623/2.11 |
| 2009/0177275 A1 | 7/2009 | Case |
| 2009/0281619 A1 | 11/2009 | Le et al. |
| 2010/0094411 A1 | 4/2010 | Tuval et al. |
| 2010/0121434 A1 | 5/2010 | Paul et al. |
| 2011/0144689 A1 | 6/2011 | Isch et al. |

FOREIGN PATENT DOCUMENTS

| | | |
|---|---|---|
| WO | 2008/138584 | 11/2008 |
| WO | 2009/091509 | 7/2009 |
| WO | 2010/121076 | 10/2010 |
| WO | 2011/035327 | 3/2011 |

* cited by examiner

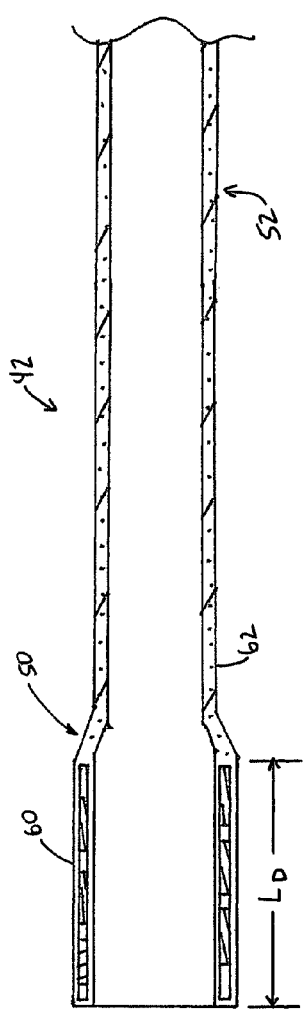
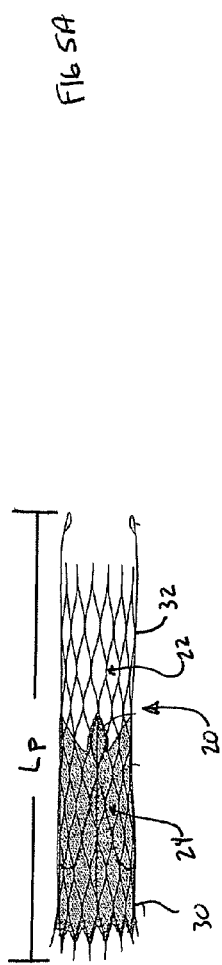
FIG 5A
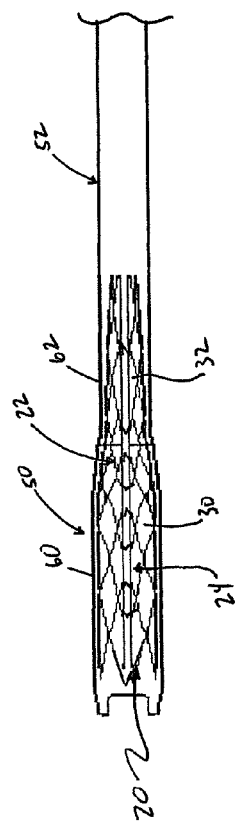
FIG 5B

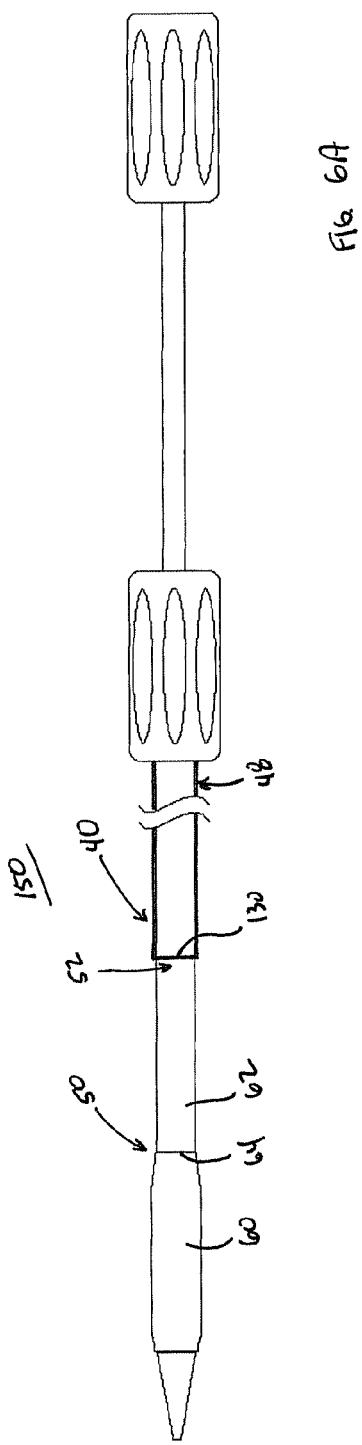
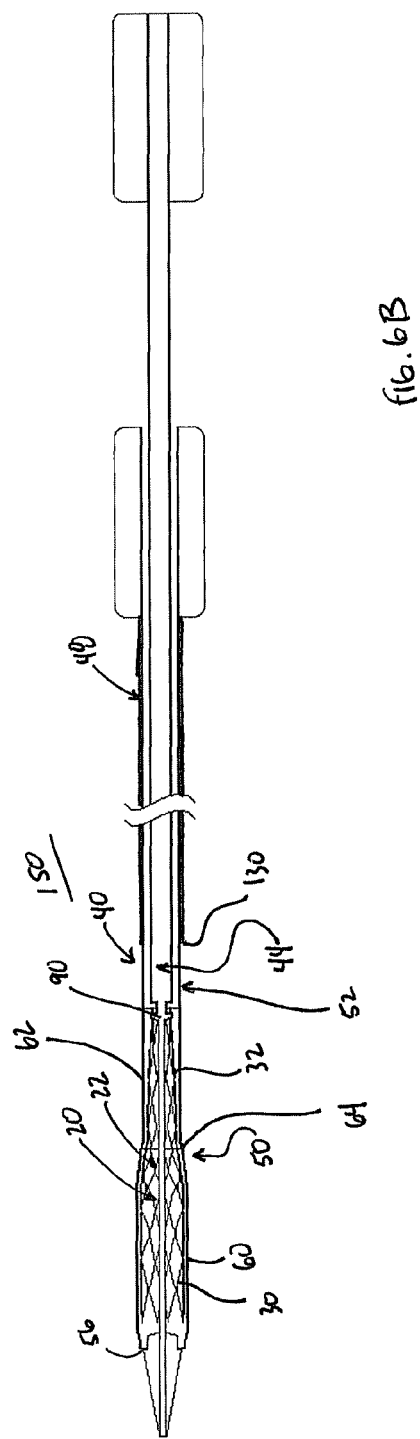
FIG. 6A
FIG. 6B

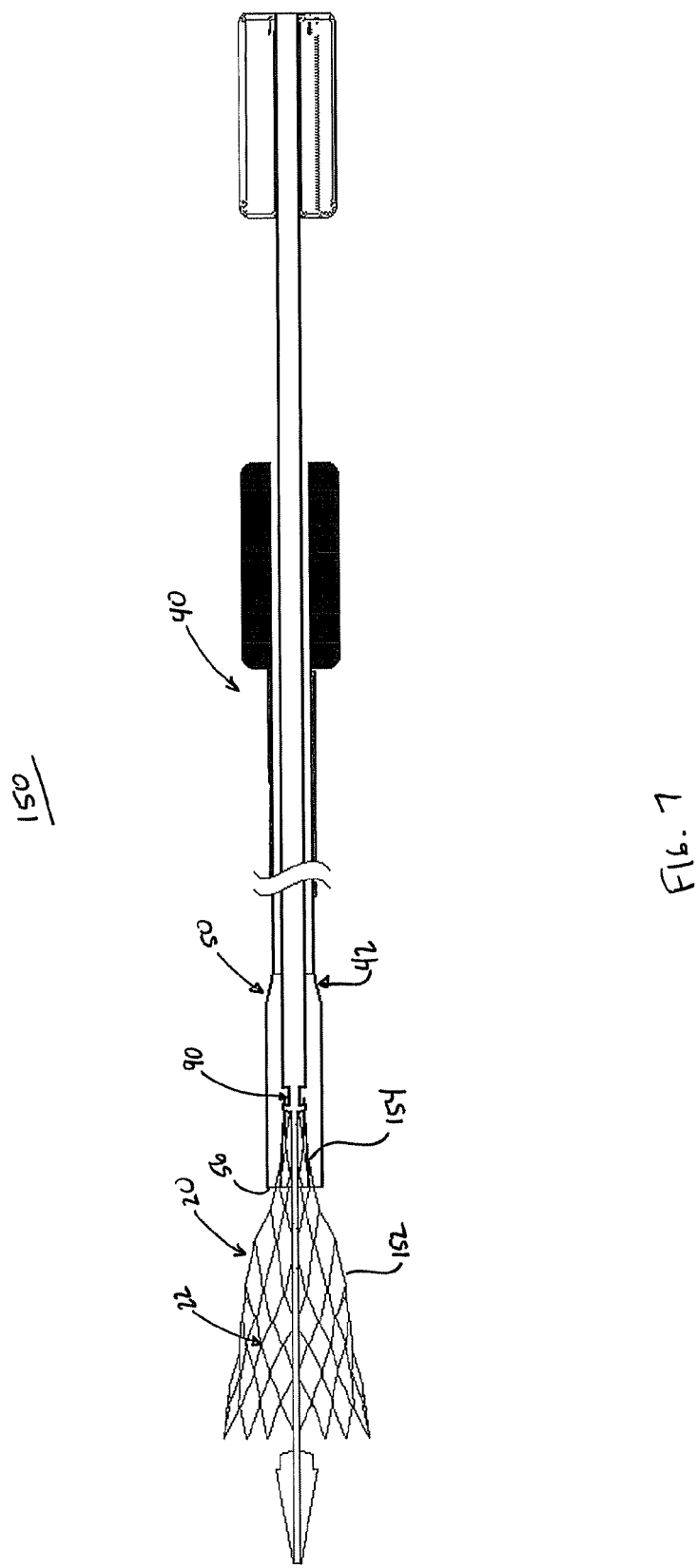

TRANSCATHETER HEART VALVE DELIVERY SYSTEM WITH REDUCED AREA MOMENT OF INERTIA

RELATED APPLICATIONS

This application is a Division of and claims the benefit of U.S. patent application Ser. No. 12/757,111 filed Apr. 9, 2010, now allowed. The disclosures of which are herein incorporated by reference in their entirety.

BACKGROUND

The present disclosure relates to systems and methods for percutaneous implantation of a heart valve prosthesis. More particular, it relates to delivery systems and methods for transcatheter implantation of a self-expanding, stented prosthetic heart valve.

Diseased or otherwise deficient heart valves can be repaired or replaced with an implanted prosthetic heart valve. Conventionally, heart valve replacement surgery is an open-heart procedure conducted under general anesthesia, during which the heart is stopped and blood flow is controlled by a heart-lung bypass machine. Traditional open surgery inflicts significant patient trauma and discomfort, and exposes the patient to a number of potential risks, such as infection, stroke, renal failure, and adverse effects associated with the use of the heart-lung bypass machine, for example.

Due to the drawbacks of open-heart surgical procedures, there has been an increased interest in minimally invasive and percutaneous replacement of cardiac valves. With these percutaneous transcatheter (or transluminal) techniques, a valve prosthesis is compacted for delivery in a catheter and then advanced, for example, through an opening in the femoral artery and through the descending aorta to the heart, where the prosthesis is then deployed in the annulus of the valve to be repaired (e.g., the aortic valve annulus). Although transcatheter techniques have attained widespread acceptance with respect to the delivery of conventional stents to restore vessel patency, only mixed results have been realized with percutaneous delivery of a relatively more complex prosthetic heart valve.

Various types and configurations of prosthetic heart valves are available, and continue to be refined. The actual shape and configuration of any particular prosthetic heart valve is dependent to some extent upon native shape and size of the valve being repaired (i.e., mitral valve, tricuspid valve, aortic valve, or pulmonary valve). In general, prosthetic heart valve designs attempt to replicate the functions of the valve being replaced and thus will include valve leaflet-like structures. With a bioprosthesis construction, the replacement valve may include a valved vein segment that is mounted in some manner within an expandable stent frame to make a valved stent (or "stented prosthetic heart valve"). For many percutaneous delivery and implantation systems, the self-expanding valved stent is crimped down to a desired size and held in that compressed state within an outer sheath, for example. Retracting the sheath from the valved stent allows the stent to self-expand to a larger diameter, such as when the valved stent is in a desired position within a patient. In other percutaneous implantation systems, the valved stent can be initially provided in an expanded or uncrimped condition, then crimped or compressed on a balloon portion of catheter until it is as close to the diameter of the catheter as possible. Once delivered to the implantation site, the balloon is inflated to deploy the so-configured prosthesis. With either of these types of percutaneous stent delivery systems, conventional sewing of the prosthetic heart valve to the patient's native tissue is typically not necessary.

It is imperative that the stented prosthetic heart valve be accurately located relative to the native annulus immediately prior to full deployment from the catheter as successful implantation requires the transcatheter prosthetic heart valve intimately lodge and seal against the native annulus. If the prosthesis is incorrectly positioned relative to the native annulus, serious complications can result as the deployed device can leak and may even dislodge from the implantation site. As a point of reference, this same concern does not arise in the context of other vascular stents; with these procedures, if the target site is "missed," another stent is simply deployed to "make-up" the difference.

While imaging technology can be employed as part of the implantation procedure to assist a clinician in better evaluating a location of the transcatheter prosthetic heart valve immediately prior to full deployment, in many instances this evaluation alone is insufficient. Instead, clinicians desire the ability to partially deploy the prosthesis, evaluate a position relative to the native annulus, and reposition the prosthesis prior to full deployment if deemed necessary. Repositioning, in turn, requires the prosthesis first be re-compressed and re-located back within the outer delivery sheath. Stated otherwise, the partially deployed, stented prosthetic heart valve must be "recaptured" by the delivery system, and in particular within the outer sheath. While, in theory, the recapturing of a partially deployed stented prosthetic heart valve is straight forward, in actual practice, the constraints presented by the implantation access path and the stented prosthetic heart valve itself render the procedure exceedingly difficult.

For example, the stented prosthetic heart valve is purposefully design to rigidly resist collapsing forces once deployed. With a self-expanding stented prosthetic heart valve, then, the stent frame must generate a high radial force when expanding from the compressed state to properly anchor itself in the anatomy of the heart. The corresponding delivery sheath segment (or capsule) compressively retaining the stented valve during delivery to the implantation site is radially stiffened to sufficiently resist radial expansion, and conventionally encompasses or surrounds an entire length of the prosthesis (i.e., while the relatively rigid capsule can be proximally coupled to a more compliant catheter shaft, the capsule itself surrounds an entirety of the prosthesis). Further, to facilitate compressed loading of the self-expanding stent frame into the outer sheath, the capsule typically has an increased inner (and outer) diameter as compared to the other, more proximal segments of the outer sheath. As part of most transcatheter heart valve replacement procedures, the delivery system (e.g., a prosthetic heart valve compressively retained within an outer sheath) must traverse the aortic arch (e.g., in a retrograde approach). While the relatively rigid, relatively large delivery sheath capsules are viable for accessing the native heart valve via the aortic arch (or other tortuous vasculature), the so-configured delivery sheath may undesirably buckle or "kink", especially when traversing the various curvatures of the aortic arch. Once kinked, it is virtually impossible for the delivery sheath capsule to be advanced over a partially-deployed prosthesis as is otherwise necessary for recapture. Simply stated, due to the relatively long stiff section of the conventional delivery sheath, successful delivery of a prosthetic heart valve through the tortuous vasculature, such as required for retrograde delivery of a prosthetic aortic heart valve, as well as recapturing a partially deployed prosthetic heart valve, has proven to be difficult.

In light of the above, although there have been advances in percutaneous valve replacement techniques and devices, there is a continued desire to provide different delivery systems for delivering cardiac replacement valves, and in particular self-expanding stented prosthetic heart valves, to an implantation site in a minimally invasive and percutaneous manner that satisfies the constraints associated with heart valve implantation (e.g., traversing the aortic arch).

SUMMARY

Some aspects in accordance with principles of the present disclosure relate to a device for repairing a heart valve of a patient. The device includes a prosthetic heart valve and a delivery system. The prosthetic heart valve has a stent frame and a valve structure. The valve structure is attached to the stent frame and forms at least two valve leaflets. Further, the prosthetic heart valve is radially self-expandable from a compressed arrangement to a natural arrangement, with the stent frame defining an axial length. The delivery system includes an inner shaft assembly and a delivery sheath. The inner shaft assembly includes an intermediate portion forming a coupling structure. The delivery sheath assembly defines a lumen sized to slidably receive the inner shaft assembly, and includes a shaft and a capsule. The capsule extends distally from the shaft and includes a distal segment and a proximal segment. An outer diameter of the capsule distal segment is greater than an outer diameter of the capsule proximal segment. Further, an axial length of the distal segment is less than the axial length of the stent frame. With this in mind, the device is configured to provide a loaded state in which the prosthetic heart valve engages the coupling structure and is compressively retained in the compressed arrangement within the capsule. In some embodiments, an inner diameter of the capsule distal segment is greater than an inner diameter of the capsule proximal segment. In other embodiments, a radial stiffness of the capsule distal segment is greater than a radial stiffness of the capsule proximal segment. In yet other embodiments, an area moment of inertia of the distal segment is greater than area moment of inertia of the proximal segment. In yet other embodiments, in the loaded state, an inflow side of the prosthetic heart valve is crimped within the distal segment of the capsule, and an outflow side of the prosthetic heart valve is crimped within the proximal segment. With these and other constructions, the capsule provides requisite resistance to radial expansion of the prosthetic heart valve, yet exhibits sufficient conformability for traversing the tortuous vasculature of the patient, for example the various curvatures of the aortic arch. For example, by providing the capsule with a lower area moment of inertia (as compared to the outer sheath capsule of a conventional self-expanding stented prosthetic heart valve delivery system), the devices of the present disclosure greatly reduce the likelihood of the capsule becoming kinked when tracking around the aortic arch. This feature, in turn, facilitates easier recapturing of the prosthetic heart valve with the capsule if desired.

Yet other aspects in accordance with principles of the present disclosure relate to a method of loading a transcatheter delivery system with a prosthetic heart valve. The prosthetic heart valve has a valve structure attached to a stent frame, and is radially self-expandable from a compressed arrangement to a natural arrangement. The method includes receiving a delivery system including an inner shaft assembly and a delivery sheath assembly. The inner shaft assembly includes an intermediate portion forming a coupling structure. The delivery sheath assembly defines a lumen sized to slidably receive the inner shaft assembly, and includes a capsule extending distally from a shaft. The capsule provides a distal segment and a proximal segment, with an outer diameter of the distal segment being greater than an outer diameter of the proximal segment. The prosthetic heart valve is disposed over the inner shaft assembly such that a proximal region of the prosthetic heart valve is adjacent the coupling structure. The prosthetic heart valve is compressed to the compressed arrangement over the inner shaft assembly by locating the capsule over the prosthetic heart valve and crimping the prosthetic heart valve into engagement with the coupling structure. In this loaded state, the distal segment of the capsule encompasses a distal region of the prosthetic heart valve, and a proximal region of the prosthetic heart valve is encompassed by the capsule proximal segment. In some embodiments, the method of loading the transcatheter delivery system includes the distal segment of the capsule encompassing an entirety of the valve structure of the prosthetic heart valve, and less than entirety of the corresponding stent frame.

Yet other aspects in accordance with principles of the present disclosure relate to a method of repairing a defective heart valve of a patient. The method includes receiving a delivery system loaded with a radially self-expanding prosthetic heart valve having a valve structure attached to a stent frame. The delivery system includes an inner shaft assembly slidably received within a delivery sheath assembly. The delivery sheath assembly provides a capsule forming a distal segment and a proximal segment, with an outer diameter of the distal segment being greater than that of the proximal segment. In this regard, the distal segment of the capsule is disposed over and compressively retains a distal region of the prosthetic heart valve, whereas the capsule proximal segment is disposed over and compressively retains a proximal region of the prosthetic heart valve such that the capsule retains the prosthetic heart valve over the inner shaft assembly in a compressed arrangement. The prosthetic heart valve is inserted into a bodily lumen while constrained within the capsule. The delivery system is manipulated to guide the prosthetic heart valve, in the compressed arrangement, through the patient's vasculature and into the defective heart valve. Finally, the capsule is withdrawn from the prosthetic heart valve to permit the prosthetic heart valve to self-expand and release from the delivery system and into engagement with the native heart valve. In some embodiments, the method includes manipulating the prosthetic heart valve around the patient's aortic arch, with the capsule not kinking when travelling across the aortic arch. In yet other embodiments, the method includes partially deploying the prosthetic heart valve from the capsule, and then recapturing the prosthetic heart valve within the capsule.

BRIEF DESCRIPTION OF THE DRAWINGS

FIG. 5A is a cross-sectional view of the delivery sheath portion of FIG. 4 along side the prosthetic heart valve of FIG. 1B;

FIG. 5B is a simplified, cross-sectional view of the delivery sheath portion and prosthetic heart valve of FIG. 5A when assembled to a loaded state;

FIG. 6A is a simplified side view of the delivery system of FIG. 2 loaded with the prosthetic heart valve of FIG. 1A to define a heart valve repair device in accordance with principles of the present disclosure;

FIG. 6B is a cross-sectional view of the device of FIG. 6A;

FIG. 7 is a simplified cross-sectional view of the device of FIG. 6A in a partially deployed state.

DETAILED DESCRIPTION

Figure 1A:
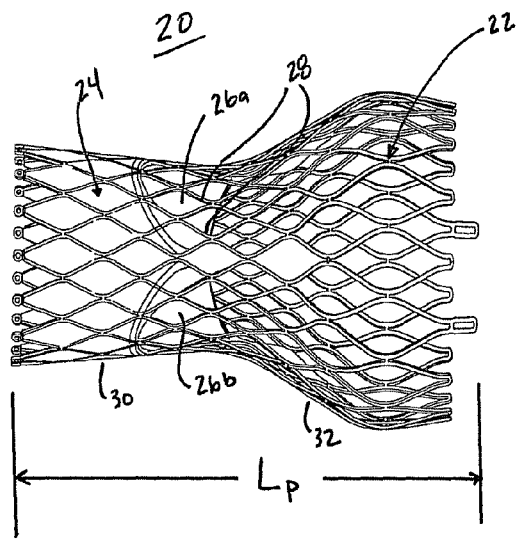
FIG. 1A is a side view of a stented prosthetic heart valve in a natural, expanded arrangement and useful with systems and methods of the present disclosure.

As referred to herein, the prosthetic heart valve as used in accordance with the various devices and methods may include a wide variety of different configurations, such as a bioprosthetic heart valve having tissue leaflets or a synthetic heart valve having a polymeric, metallic, or tissue-engineered leaflets, and can be specifically configured for replacing any heart valve. Thus, the prosthetic heart valve useful with the devices and methods of the present disclosure can be generally used for replacement of a native aortic, mitral, pulmonic, or tricuspid valves, for use as a venous valve, or to replace a failed bioprosthesis, such as in the area of an aortic valve or mitral valve, for example.

In general terms, the prosthetic heart valves of the present disclosure include a stent or stent frame maintaining a valve structure (tissue or synthetic), with the stent having a normal, expanded arrangement or state and collapsible to a compressed arrangement for loading within the delivery system. The stent is normally constructed to self-deploy or self-expand when released from the delivery system. For example, the stented prosthetic heart valve useful with the present disclosure can be a prosthetic valve sold under the trade name CoreValve® available from Medtronic CoreValve, LLC. Other non-limiting examples of transcatheter heart valve prostheses useful with systems and methods of the present disclosure are described in U.S. Publication Nos. 2006/0265056; 2007/0239266; and 2007/0239269, the teachings of each of which are incorporated herein by reference. The stents or stent frames are support structures that comprise a number of struts or wire portions arranged relative to each other to provide a desired compressibility and strength to the prosthetic heart valve. In general terms, the stents or stent frames of the present disclosure are generally tubular support structures having an internal area in which valve structure leaflets will be secured. The leaflets can be formed from a verity of materials, such as autologous tissue, xenograph material, or synthetics as are known in the art. The leaflets may be provided as a homogenous, biological valve structure, such as porcine, bovine, or equine valves. Alternatively, the leaflets can be provided independent of one another (e.g., bovine or equine paracardial leaflets) and subsequently assembled to the support structure of the stent frame. In another alternative, the stent frame and leaflets can be fabricated at the same time, such as may be accomplished using high-strength nano-manufactured NiTi films produced at Advance BioProsthetic Surfaces (ABPS), for example. The stent frame support structures are generally configured to accommodate at least two, alternatively three, leaflets; however, replacement prosthetic heart valve of the types described herein can incorporate more or less than three leaflets.

Some embodiments of the stent frames can be a series of wires or wire segments arranged such that they are capable of self-transitioning from a collapsed arrangement to a normal, radially expanded arrangement. In constructions, a number of individual wires comprising the stent frame support structure can be formed of a metal or other material. These wires are arranged in such a way that the stent frame support structure allows for folding or compressing or crimping to the compressed arrangement in which its internal diameter is smaller than its internal diameter when in the natural, expanded arrangement. In the collapsed arrangement, such a stent frame support structure with attached valves can be mounted onto a delivery system. The stent frame support structures are configured so that they can be changed to their natural, expanded arrangement when desired, such as by the relative movement of one or more sheaths relative to a length of the stent frame.

The wires of the stent frame support structures in embodiments of the present disclosure can be formed from a shape memory material such as a nickel titanium alloy (e.g., Nitinol™). With this material, the support structure is self-expandable from the compressed arrangement to the natural, expanded arrangement, such as by the application of heat, energy, and the like, or by the removal of external forces (e.g., compressive forces). This stent frame support structure can also be compressed and re-expanded multiple times without damaging the structure of the stent frame. In addition, the stent frame support structure of such an embodiment may be laser-cut from a single piece of material or may be assembled from a number of different components. For these types of stent frame structures, one example of a delivery system that can be used includes a catheter with a retractable sheath that covers the stent frame until it is to be deployed, at which point the sheath can be retracted to allow the stent frame to self-expand. Further details of such embodiments are discussed below.

Figure 1B:
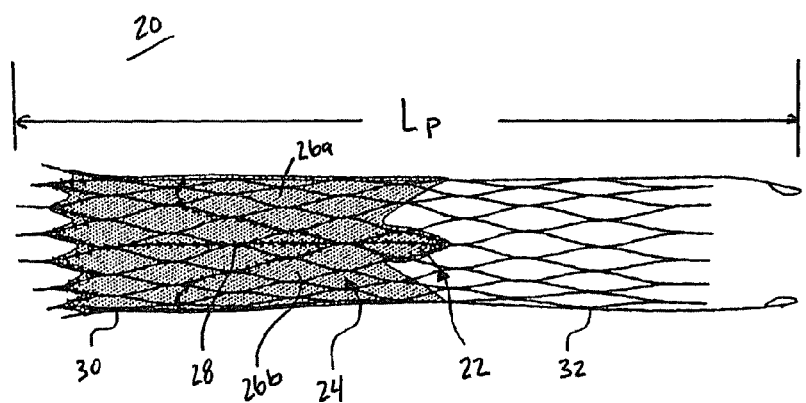
FIG. 1B is a side view of the prosthesis of FIG. 1A in a compressed arrangement.

With the above understanding in mind, one non-limiting example of a stented prosthetic heart valve 20 useful with devices and methods of the present disclosure is illustrated in FIG. 1A. As a point of reference, the prosthetic heart valve 20 is shown in a natural or expanded arrangement in the view of FIG. 1A; FIG. 1B illustrates the prosthetic heart valve 20 in a compressed arrangement (e.g., when compressively retained within an outer tube or sheath). The prosthetic heart valve 20 includes a stent or stent frame 22 and a valve structure 24. The stent frame 22 can assume any of the forms described above, and is generally constructed so as to be self-expandable from the compressed arrangement (FIG. 1B) to the natural, expanded arrangement (FIG. 1A). The valve structure 24 is assembled to the stent frame 22 and forms or provides two or more (typically three) leaflets 26a, 26b. The valve structure 24 can assume any of the forms described above, and can be assembled to the stent frame 22 in various manners, such as by sewing the valve structure 24 to one or more of the wire segments 28 defined by the stent frame 22.

With the but one acceptable construction of FIGS. 1A and 1B, the prosthetic heart valve 20 is configured for repairing an aortic valve. Alternatively, other shapes are also envisioned to adapt to the specific anatomy of the valve to be repaired (e.g., stented prosthetic heart valves in accordance with the present disclosure can be shaped and/or sized for replacing a native mitral, pulmonic, or tricuspid valve). Regardless, the stent frame 22 defines an axial length $L_P$ of the prosthetic heart valve 20. With the one construction of FIGS. 1A and 1B, the valve structure 24 extends less than the entire length $L_P$ of the stent frame 22. In particular, the valve structure 24 is assembled to, and extends along, an inflow region 30 of the prosthetic heart valve 20, whereas an outflow region 32 is free of the valve structure 24 material. As a point of reference, "inflow" and "outflow" terminology is in reference to an arrangement of the prosthetic heart valve 20 upon final implantation relative to the native aortic valve (or other valve) being repaired. A wide variety of constructions are also acceptable and within the scope of the present disclosure. For example, in other embodiments, the valve structure 24 can extend along an entirety, or a near entirety, of a length of the stent frame 22.

Figure 2:
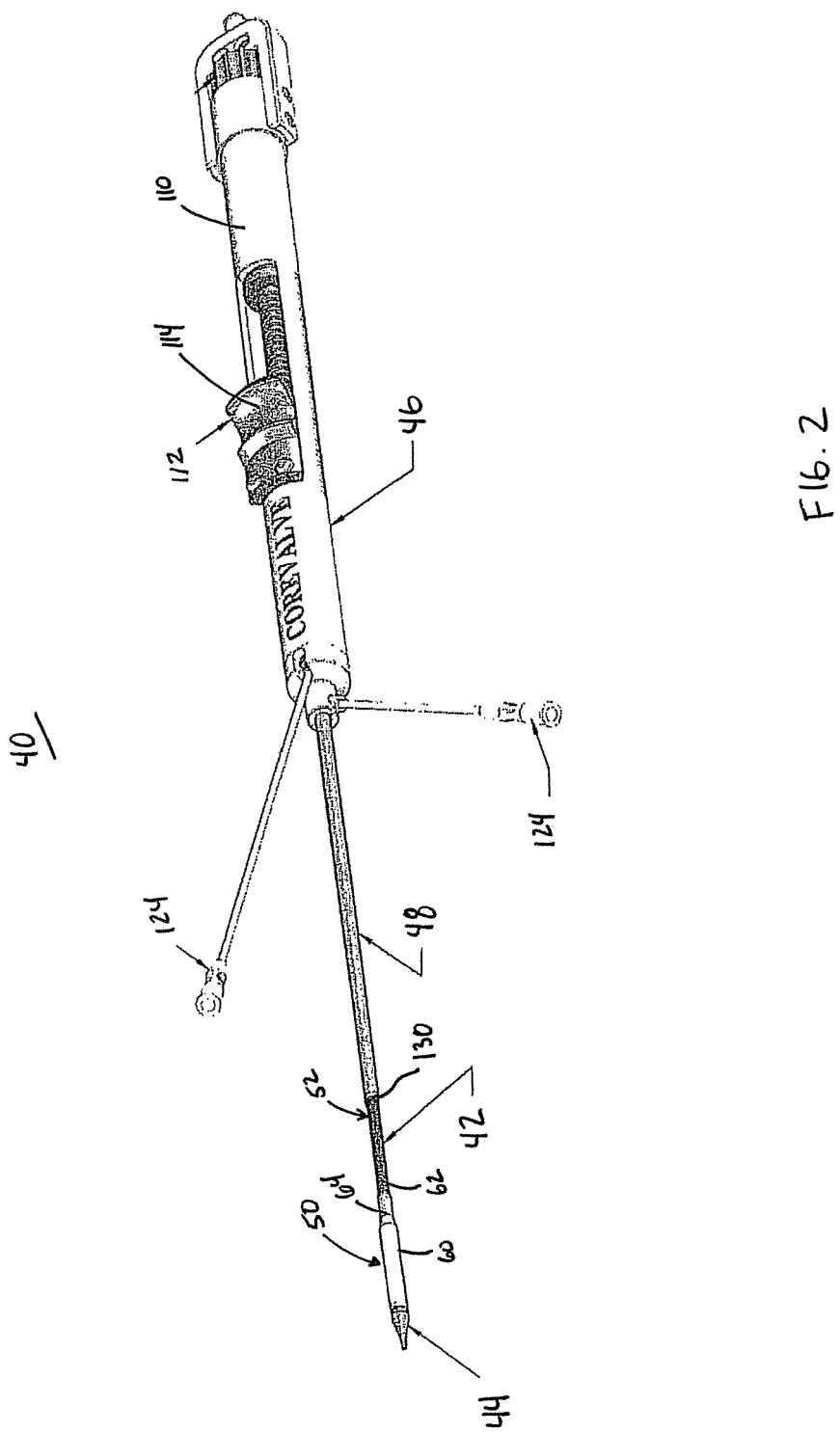
FIG. 2 is a perspective view of a delivery system in accordance with principles of the present disclosure and useful for percutaneously delivering the prosthetic heart valve of FIGS. 1A and 1B to a heart valve implantation site.

With the above understanding of the prosthetic heart valve 20 in mind, one embodiment of a delivery system 40 in accordance with the present disclosure is shown in FIG. 2. As a point of reference, although the delivery system 40 can be loaded with a stented prosthetic heart valve for percutaneous delivery thereof, such a prosthesis is not visible in the view of FIG. 2. The delivery system 40 includes a delivery sheath assembly 42, an inner shaft assembly 44 (referenced generally), a handle 46, and an optional outer stability tube 48. Details on the various components are provided below. In general terms, however, the delivery system 40 is transitionable from a loaded state (shown in FIG. 2) in which the stented prosthetic heart valve is contained within a capsule 50 of the delivery sheath assembly 42, to a deployed state in which the capsule 50 is retracted from the prosthetic heart valve, thereby permitting the prosthetic heart valve to self-expand (or alternatively be caused to expand by a separate mechanism such as a balloon) and release from the delivery system 40. In this regard, an actuator mechanism (described below) can be provided with the handle 46 that facilitates transitioning from the loaded state to the deployed state, operating to proximally retract the delivery sheath assembly 42, and in particular the capsule 50, from over the prosthetic heart valve. The delivery system 40 can be used with a conventional introducer device (not shown), with the optional outer stability tube 48, where provided, serving to frictionally isolate the delivery sheath assembly 42 from the introducer device.

Figure 3:
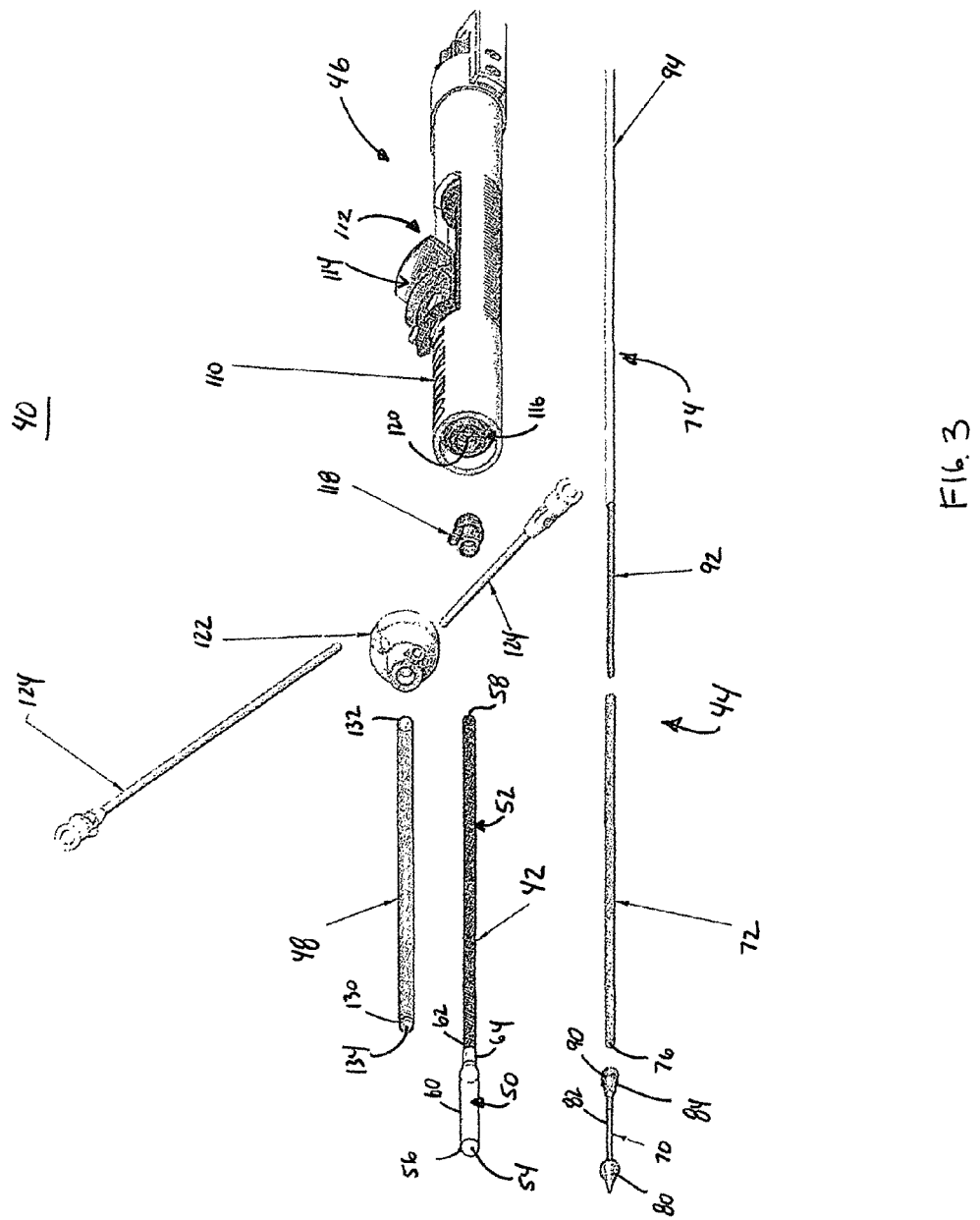
FIG. 3 is a perspective, exploded view of the delivery system of FIG. 2.

Representative configurations of the components 42-48 in accordance with some embodiments of delivery systems encompassed by the present disclosure are shown in greater detail in FIG. 3. In this regard, various features illustrated in FIG. 3 can be modified or replaced with differing structures and/or mechanisms. Thus, the present disclosure is in no way limited to the inner shaft assembly 44, the handle 46, etc., as shown and described below. In more general terms, then, delivery systems in accordance with principles of the present disclosure provide features capable of compressively retaining a self-expanding, stented prosthetic heart valve (e.g., the delivery sheath capsule 50), along with one or more mechanisms capable of effectuating release or deployment of the heart valve prosthesis from the delivery system.

The delivery sheath assembly 42 includes the capsule 50 and a shaft 52, and defines a lumen 54 (referenced generally) extending from a distal end 56 to a proximal end 58. The capsule 50 is attached to, and extends distally from, the shaft 52.

Figure 4:
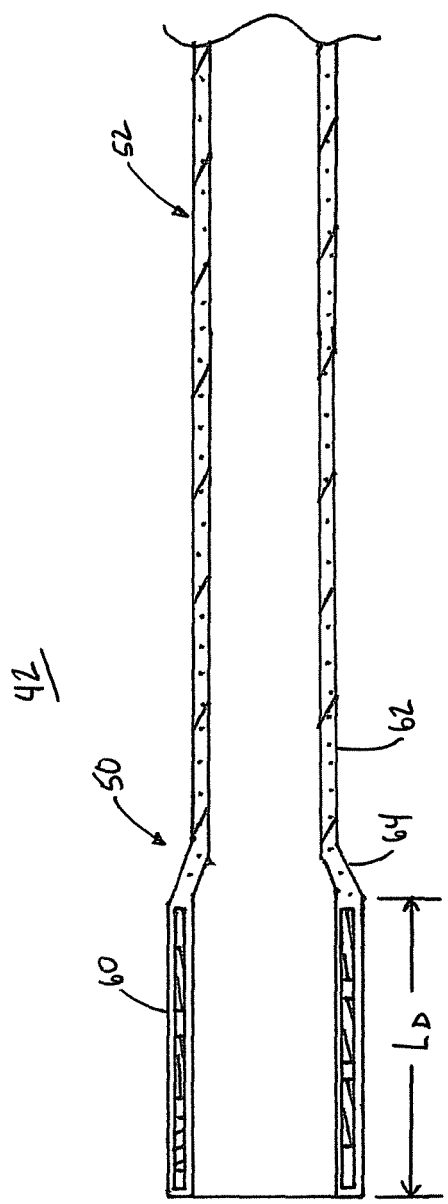
FIG. 4 is an enlarged, cross-sectional view of a portion of a delivery sheath assembly component of the delivery system of FIG. 2.

The capsule 50 is constructed to compressively retain the self-expanding, stented prosthetic heart valve, and includes or defines a distal segment 60 and a proximal segment 62. The distal segment 60 can terminate at the distal end 56 of the delivery sheath assembly 52; in other embodiments, an additional tubular structure is provided distal the distal segment 60 (e.g., polymer tubing carrying a radiopaque marker) that is not intended or constructed to compressively retain the prosthetic heart valve 20 (FIG. 1B) in the loaded state, and thus is not part of the capsule 50. With additional reference to FIG. 4, the proximal segment 62 can be formed as a continuation of the shaft 52. Alternatively, the proximal segment 62 and the shaft 52 can have differing constructions. Regardless, construction of the distal segment 60 differs from that of the proximal segment 62 so as to generate a connection point or intermediate zone 64 between the segments 60, 62. Further, an axial length $L_D$ of at least the distal segment 60 selected in accordance with the axial length $L_P$ (FIGS. 1A and 1B) of the prosthetic heart valve 20 to be loaded within the system 40 as described below.

The differing constructions of the distal and proximal segment 60, 62 can assume various forms. For example, in some constructions, an outer diameter of the distal segment 60 is greater than an outer diameter of the proximal segment 62. Further, an inner diameter of the distal segment 60 can be greater than an inner diameter of the proximal segment 62. Alternatively or in addition, a radial stiffness of the distal segment 60 can be greater than a radial stiffness of the proximal segment 62. Even further, an area moment of inertia of the distal segment 60 can be greater than an area moment of inertia of the proximal segment 62. As a point of reference, the area moment of inertia of the capsule segments 60, 62 (also known as second moment of inertia) is a property of the shape of the capsule segment 60, 62, and can be used to predict the deflection and conformability to the shape of the tortuous vasculature through which the capsule 50 is directed. One such vasculature region is the aortic arch; the conformability of the capsule 50 to the aortic arch depends on the geometry of the cross-section of the capsule segment 60, 62. Lowering the area moment of inertia of the capsule 50 as a whole (e.g., configuring the proximal segment 62 with a lower area moment of inertia than the distal segment 60 results in the capsule 50 collectively having a reduced area moment of inertia as compared to a conventional, entirely uniform capsule construction) will lessen the likelihood that the capsule 50 will kink when advanced through the aortic arch.

In some embodiments, the distal segment 60 is a cut metal tube (e.g., a laser-cut hypotube) embedded or encapsulated within a polymer (e.g., Pebax®), whereas the proximal segment 62 is a braided polymer tube. A variety of other constructions are also acceptable so long as the distal segment 60 has one or more of a greater outer diameter, inner diameter, area moment of inertia, or stiffness as compared to the proximal segment 62, and the capsule segments 60, 62 each exhibit sufficient radial or circumferential rigidity so as to overtly resist the expected expansive forces associated with the corresponding region of the stented prosthetic heart valve to be compressively held within the capsule 50. Thus, for example, the distal and proximal segment 60, 62 can be formed of a similar material (e.g., a polymer tube, braided tube, etc.). Other acceptable constructions of the capsule 50 include high strength polymeric materials (e.g., polyamide, PEEK, etc.).

FIG. 5A illustrates a relationship between the axial length $L_D$ of the capsule distal segment 60 and the axial length $L_P$ of the prosthetic heart valve 20. In particular, the capsule distal segment axial length $L_D$ is less than the prosthetic heart valve axial length L. As a point of clarification, with embodiments in which the proximal segment 62 is formed or defined as a homogenous continuation of the delivery sheath shaft 52, a perceptible demarcation between the proximal segment 62 and the shaft 52 will not exist. When loaded with the prosthetic heat valve 20, however, a portion of the shaft 52 will reside over a region of the prosthetic heart valve 20 and can be viewed as defining the proximal segment 62 of the capsule 50. As best shown in FIG. 5B, upon loading of the prosthetic heart valve 20 (in the compressed arrangement) within the capsule 50, the distal segment 60 extends over or encompasses less than an entirety of the prosthetic heart valve 20, for example less than an entirety of the stent frame 22. In some constructions, the capsule distal segment axial length $L_D$ is slightly greater than the length of the valve structure 24 such that the valve structure 24 is within the distal segment 60 in the loaded state, with a remainder of the stent frame 22 being within the proximal segment 62. In yet other embodiments, the capsule distal segment axial length $L_D$ is selected such that in the loaded state, the inflow region 30 of the prosthetic heart valve 20 is within the distal segment 60, and the outflow region 32 is within the proximal segment 62. Regardless, unlike conventional transcatheter delivery system configurations in which the stiffer, increased outer diameter portion of the delivery sheath is sized to encompass an entirety of the prosthetic heart valve when loaded, the stiffer/larger distal segment 60 associated with the delivery system 40 of the present disclosure has a reduced length that is less than a length of the selected prosthetic heart valve 20.

Returning to FIGS. 2 and 3, the shaft 52 extends proximally from the capsule 50, and can be formed as a braided tube. For example, the shaft 52 can be a thermoplastic elastomer, such as Pebax®, with an embedded braided metal layer constructed from stainless steel wire. Other configurations are also acceptable, with the shaft 52 serving to connect the capsule 50 with the handle 46. As described above, and in some constructions, the proximal segment 62 of the capsule 50 is defined as a continuation of the shaft 52, with the shaft 52 being coupled to the distal segment 60 at the connection point 64 (e.g., heat or adhesive bonding). The shaft 52 is constructed to be sufficiently flexible for passage through a patient's vasculature yet exhibits sufficient longitudinal rigidity to effectuate desired axial movement of the capsule 50. In other words, proximal retraction of the proximal end 58 of the shaft 52 is directly transferred to the capsule 50 and causes a corresponding proximal retraction of the capsule 50. In some embodiments, the shaft 52 is further configured to transmit a rotational force or movement onto the capsule 50.

The inner shaft assembly 44 can assume a variety of forms appropriate for supporting a stented prosthetic heart valve within the capsule 50. For example, the inner shaft assembly 44 can include a retention member 70, an intermediate tube 72, and a proximal tube 74. In general terms, the retention member 70 is akin to a plunger, and incorporates features for retaining the stented prosthetic heart valve within the capsule segment 50 as described below. The intermediate tube 72 connects the retention member 70 to the proximal tube 74, with the proximal tube 74, in turn, coupling the inner shaft assembly 44 with the handle 46. The components 70-74 can combine to define a continuous lumen 76 (referenced generally) sized to slidably receive an auxiliary component such as a guide wire (not shown).

The retention member 70 can include a tip 80, a support tube 82, and a hub 84. The tip 80 forms or defines a nose cone having a distally tapering outer surface adapted to promote atraumatic contact with bodily tissue. The tip 80 can be fixed or slidable relative to the support tube 82. The support tube 82 extends proximally from the tip 80 and is configured to internally support a compressed, stented prosthetic heart valve generally disposed thereover, and has a length and outer diameter corresponding with dimensional attributes of the prosthetic heart valve. The hub 84 is attached to the support tube 82 opposite the tip 80 (e.g., adhesive bond), and provides a coupling structure 90 (referenced generally) configured to selectively capture a corresponding feature of the prosthetic heart valve. The coupling structure 90 can assume various forms, and is generally located along an intermediate portion of the inner shaft assembly 44. In some embodiments, the coupling structure 90 includes one or more fingers sized to be received within corresponding apertures formed by the prosthetic heart valve stent frame (e.g., the prosthetic heart valve stent frame can form wire loops at a proximal end thereof that are received over respective ones of the fingers when compressed within the capsule 50).

The intermediate tube 72 is formed of a flexible material (e.g., PEEK), and is sized to be slidably received within the delivery sheath assembly 40, and in particular the shaft 52. The proximal tube 74 can include a leading portion 92 and a trailing portion 94. The leading portion 92 serves as a transition between the intermediate and proximal tubes 72, 74, and thus a flexible tubing (e.g., PEEK) having a diameter slightly less than that of the intermediate tube 72. The trailing portion 94 has a more rigid construction, configured for robust assembly with the handle 46. For example, in some constructions, the trailing portion 94 is a metal hypotube. Other constructions are also acceptable. For example, in other embodiments, the intermediate and proximal tubes 72, 74 are integrally formed as a single, homogenous tube or solid shaft.

The handle 46 generally includes a housing 110 and an actuator mechanism 112 (referenced generally). The housing 110 maintains the actuator mechanism 112, with the actuator mechanism 112 configured to facilitate sliding movement of the delivery sheath assembly 42 relative to the inner shaft assembly 44, as well as the outer stability tube 48 (where provided). The housing 110 can have any shape or size appropriate for convenient handling by a user. In one simplified construction, the actuator mechanism 112 includes a user interface or actuator 114 slidably retained by the housing 110 and coupled to a sheath connector body 116. The proximal end 58 of the delivery sheath assembly 42 is coupled to the sheath connector body 116 (e.g., via an optional mounting boss 118 in some embodiments). The inner shaft assembly 44, and in particular the proximal tube 74, is slidably received within a passage 120 of the sheath connector body 116, and is rigidly coupled to the housing 110. Sliding of the actuator 114 relative to the housing 110 thus causes the delivery sheath assembly 42 to move or slide relative to the inner shaft assembly 44, for example to effectuate deployment of a prosthesis from the inner shaft assembly 44. A cap 122 can be provided for attaching the optional outer stability tube 48 to the housing 110 (such that the delivery sheath assembly 42 is slidable relative to the outer stability tube 48 with movement of the actuator 114), and can be configured to accommodate one or more optional port assemblies 124. In other embodiments, the outer stability tube 48 can be moveably coupled to the housing 110 in a manner permitting selective sliding of the outer stability tube 48 relative to the delivery sheath assembly 42 (and vice-versa). In yet other embodiments, the outer stability tube 48 can be eliminated, such that the cap 122 is omitted. Similarly, the actuator mechanism 112 can assume a variety of other forms differing from those implicated by the illustration of FIG. 3.

Where provided, the outer stability tube 48 serves as a stability shaft for the delivery system 40, and defines a distal end 130, a proximal end 132, and a passageway 134 (referenced generally) extending between, and fluidly open at, the ends 130, 132. The passageway 134 is sized to coaxially receive the delivery sheath assembly 42, and in particular the shaft 52, in a manner permitting sliding of the shaft 52 relative to the outer stability tube 48. Stated otherwise, an inner diameter of the outer stability tube 48 is slightly greater than an outer diameter of the shaft 52. As described in greater detail below, the outer stability tube 48 has a length selected to extend over a significant (e.g., at least a majority, and in other embodiments, at least 80%) of a length of the shaft 52 in distal extension from the handle 46. Further, the outer stability tube 48 exhibits sufficient radial flexibility to accommodate passage through a patient's vasculature (e.g., the femoral artery, aortic arch, etc.).

FIGS. 6A and 6B illustrate, in simplified form, assembly of the prosthetic heart valve 20 with the delivery system 40 in defining a device 150 for repairing a defective heart valve. For ease of illustration, the valve structure 24 (FIGS. 1A and 1B) is omitted, and only the stent frame 22 is shown. The prosthetic heart valve 20 is disposed over the inner shaft assembly 44, with the proximal region (e.g., outflow region) 32 being crimped into engagement with the coupling structure 90. The capsule 50 is slidably disposed over the prosthetic heart valve 20, compressively retaining the prosthetic heart valve 20 about the inner shaft assembly 44. In the loaded state of FIG. 6B, the distal end 56 of the capsule 50 is positioned immediately distal the prosthetic heart valve 20, with the distal segment 60 encompassing a portion, but not an entirety, of the prosthetic heart valve 20. Thus, the connection point or intermediate zone 64 of the capsule 50 is radially over the prosthetic heart valve 20. For example, and as described above, the capsule 50 can be configured such that the distal segment 60 encompasses the distal region (e.g., inflow region) 30 of the prosthetic heart valve 20, whereas the capsule proximal segment 62 encompasses the proximal region (e.g., outflow region) 32. In some embodiments, where the distal segment 60 has a larger inner diameter than that of the proximal segment 62, the prosthetic heart valve 20 can more easily be loaded within the capsule 50 and crimped relative to the inner shaft assembly 44 with configurations in which the inflow region 30 exhibits a greater resistance to radial compression as compared to the resistance exhibited by the outflow region 32. For example, with constructions of the prosthetic heart valve 20 in which the valve structure 24 (FIGS. 1A and 1B) extends along only the inflow region 30 such that the outflow region 32 is free of the valve structure material, the inflow region 30 will more overtly resist radially inward compression as compared to the outflow region 32; under these circumstances, by providing the distal segment 60 with an increased inner diameter as compared to the proximal segment 62, the prosthetic heart valve 20 can more readily be loaded within the capsule 50.

Figure 6C:
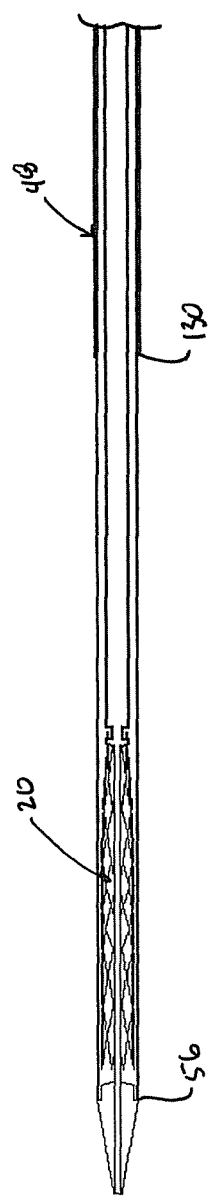
FIG. 6C is a simplified, cross-sectional view of a prior transcatheter prosthetic heart valve delivery system loaded with a prosthetic heart valve.

FIGS. 6A and 6B further illustrate the optional outer stability tube 48, including a location of the distal end 130 thereof relative to the capsule 50 and the prosthetic heart valve 20. In some constructions where the outer stability tube 48 is sized to have as great a length/distal extension as possible for supporting the delivery sheath assembly 42, the distal end 130 is located along the shaft 52 (in the loaded state) at a proximal spacing from the distal end 56 by a distance that is less than twice the axial length of the capsule 50. Stated otherwise, the distal end 130 of the outer stability tube 48 can be located at a proximal spacing from the connection point 64 approximately equal to a length of the distal segment 60 (and any additional delivery sheath body distal the distal segment 60 where included). As a point of reference, with conventional transcatheter heart valve delivery systems having a stiff delivery sheath capsule encompassing an entire length of the prosthetic heart valve, the distal end 130 of the outer stability tube 48 is proximally spaced from the capsule distal end 56 by a distance sufficient to permit complete withdrawal of the capsule from over the prosthetic heart valve 20 without any portion of the capsule entering the outer stability tube 48. FIG. 6C illustrates this prior art arrangement. A comparison of FIGS. 6B and 6C reveals that with the delivery system 40 of the present disclosure, the distal end 130 of the outer stability tube 48 can extend distally further as compared to prior delivery system arrangements.

The device 150 can be transitioned to a deployed state by withdrawing the capsule 50 from the prosthetic heart valve 20, as partially reflected in FIG. 7. As a point of reference, in the view of FIG. 7, the capsule 50 has been partially, but not completely, withdrawn from over the prosthetic heart valve 20. As shown, a distal region 152 of the prosthetic heart valve 20 is exteriorly exposed relative to the capsule 50 and self-transitions toward the natural, expanded arrangement, while a proximal region 154 remains within the capsule 50, engaged with the coupling structure 90. With further proximal retraction of the capsule 50 from the arrangement of FIG. 7 until the distal end 56 of delivery sheath assembly 42/capsule 50 is proximal the prosthetic heart valve 20, the prosthetic heart valve 20 will fully self-expand, and release from the delivery system 40. Under circumstances where the clinician desires to reposition the prosthetic heart valve 20 relative to a desired implantation site, the delivery system 40 can alternatively be transitioned from the partially deployed state of FIG. 7 and back to the loaded state of FIG. 6A by distally advancing the capsule 50 back over the distal region 152 of the prosthetic heart valve 20, thereby compressing the stent frame 22 and recapturing the prosthetic heart valve 20 relative to the delivery system 40. In this regard, due to the lower area moment of inertia exhibited by the capsule 50 as compared to prior transcatheter, self-expanding heart valve delivery sheaths, the capsule 50 is unlikely to experience kinking when traversing through the patient's vasculature, thus enhancing the likelihood that the capsule 50 will have sufficient structural integrity to effectuate recapture.

Figure 8A:
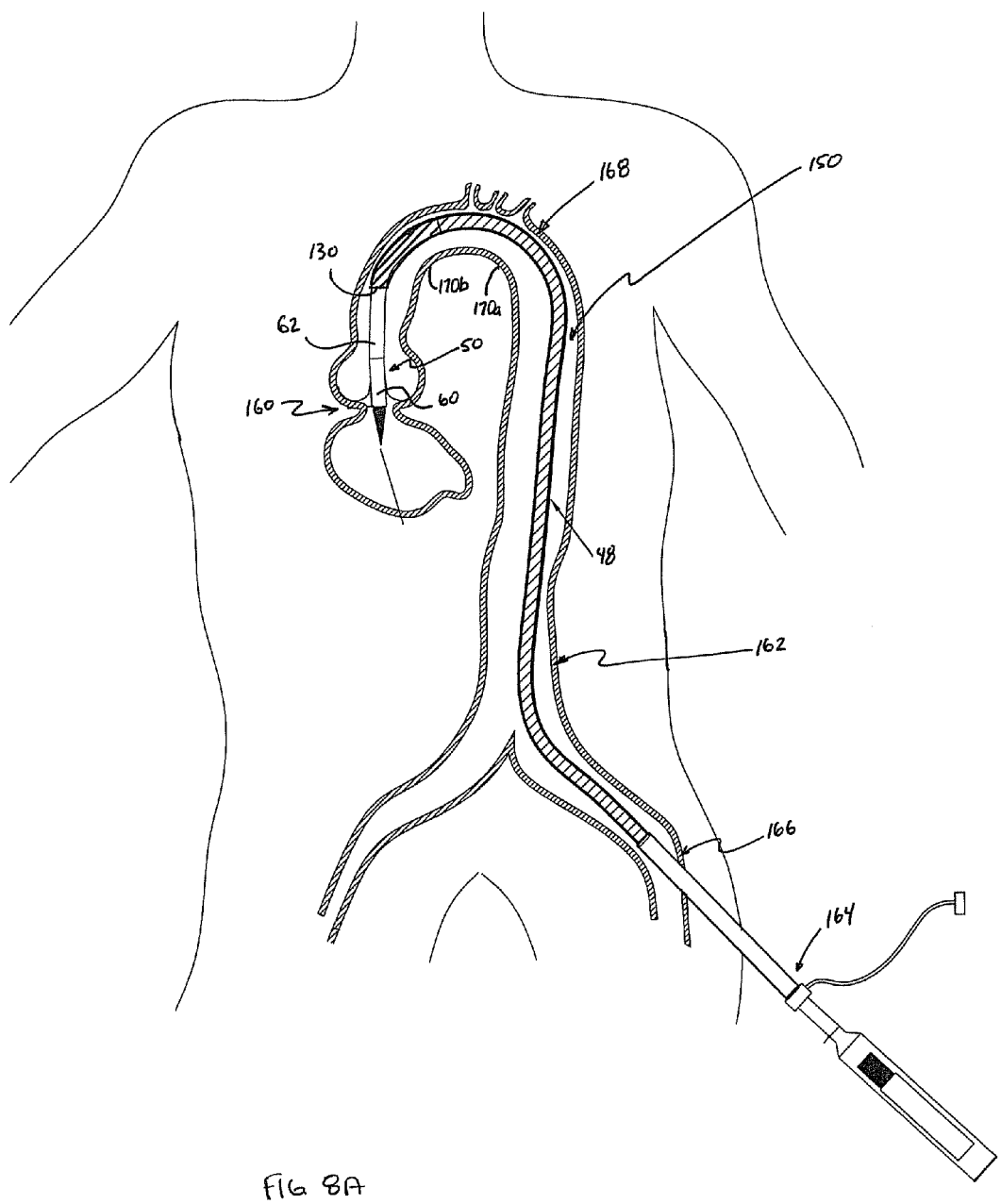
FIGS. 8A and 8B illustrate use of the device of FIG. 6A in percutaneously delivering the prosthetic heart valve to an aortic valve implantation site via an aortic arch of the patient.
Figure 8B:
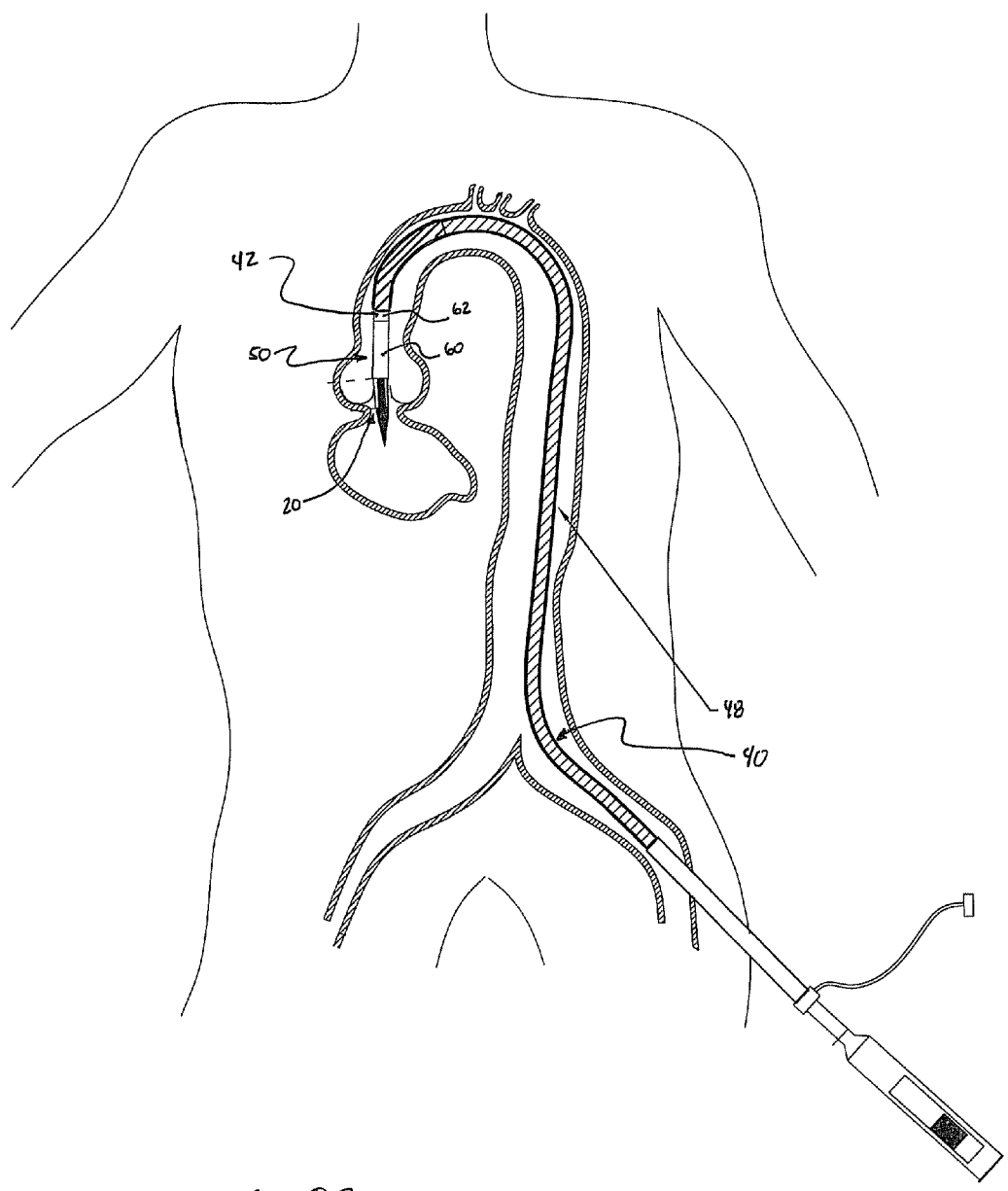

As indicated above, the delivery system 40 is well-suited for percutaneously delivering the prosthetic heart valve 20 to various native valves. One such procedure is schematically reflected in FIG. 8A in which the device 150 is employed to repair a defective aortic valve 160. As shown, the device 150 (in the loaded state) is introduced into the patient's vasculature 162 (referenced generally) via an introducer device 164. The introducer device 164 provides a port or access to a femoral artery 166. From the femoral artery 166, the capsule 50 (that otherwise compressively retains the prosthetic heart valve 20 (FIG. 6A)) is advanced via a retrograde approach through an aortic arch 168 (e.g., via iliac arteries). In this regard, the aortic arch 168 forms several small radius of curvature bends 170a, 170b. In these small radius of curvature bends 170a, 170b, kinking of the capsule 50 is most likely to occur. While the increased outer diameter and/or elevated stiffness of the distal segment 60 may have an increased propensity for buckling or kinking along the small radius of curvature bends 170a, 170b, by shortening a length of the distal segment 60 as compared to conventional designs, the likelihood of kinking when tracking along the aortic arch 168 is reduced. While the proximal segment 62 is located adjacent the second bend 170b in the final implantation position of FIG. 8A, the reduced outer diameter and/or area moment of inertia associated with the proximal segment 62 is less likely to experience buckling. Finally, FIG. 8A reflects the optional outer stability tube 48 extending along a substantial length of the delivery sheath assembly 42, with the distal end 130 being fairly proximate the capsule 50. FIG. 8B schematically illustrates deployment of the prosthetic heart valve 20 from the delivery system 40 via proximal retraction of the delivery sheath assembly 42, and in particular the capsule 50. A comparison of FIGS. 8A and 8B reveals that in the deployed state of FIG. 8B, the proximal segment 62 of the capsule 50 is retracted within the optional outer stability tube 48.

The devices, systems, and methods of the present disclosure provide a marked improvement over previous designs. By providing the delivery sheath capsule with a shortened segment of increased diameter and/or stiffness, a wall thickness of the capsule is minimized (as compared to conventional stented, self-deploying prosthetic heart valve delivery system designs), thus minimizing the potential for kinking that in turn promotes recaptureability of the prosthetic heart valve. Further, an overall profile of the delivery system is reduced. The inner diameter of the capsule distal segment can be increased for easier prosthetic heart valve loading and deployment, and a stiffer material can be used for the capsule distal segment without sacrificing trackability. Finally, with embodiments in which an optional outer stability tube is employed, the distal end of the stability tube can be distally closer to the distal end of the sheath capsule, and thus can improve deployment accuracy around the aortic arch.

Although the present disclosure has been described with reference to preferred embodiments, workers skilled in the art will recognize that changes can be made in form and detail without departing from the spirit and scope of the present disclosure.

What is claimed is:

1. A method of loading a transcatheter delivery system with a prosthetic heart valve having a stent frame and a valve structure assembled to the stent frame and forming at least two valve leaflets, the prosthetic heart valve being radially self-expandable from a compressed arrangement to a natural arrangement, the method comprising:
   receiving a delivery system including:
   an inner shaft assembly including an intermediate portion forming a coupling structure,
   a delivery sheath assembly defining a lumen sized to slidably receive the inner shaft assembly and including a shaft and a capsule extending distally from the shaft, the capsule including a distal segment and a proximal segment, wherein an outer diameter of the distal segment is greater than an outer diameter of the proximal segment; and an axial length of the distal segment is less than an axial length of the stent frame;
   coaxially disposing the prosthetic heart valve over the inner shaft assembly such that a proximal region of the prosthetic heart valve is adjacent the coupling structure; and
   compressing the prosthetic heart valve to the compressed arrangement over the inner shaft assembly, including disposing the capsule segments over the prosthetic heart valve and crimping the prosthetic heart valve into engagement with the coupling structure to achieve a loaded state;
   wherein the loaded state includes the distal segment encompassing and contacting a distal region of the prosthetic heart valve and the proximal segment encompassing and contacting a proximal region of the prosthetic heart valve; wherein the prosthetic heart valve is entirely compressibly retained within the proximal and distal segments.

2. The method of claim 1, wherein the distal region of the prosthetic heart valve is an inflow region and the proximal region is an outflow region.

3. The method of claim 1, wherein the loaded state includes the distal segment encompassing an entirety of the valve structure and less than an entirety of the stent frame.

4. The method of claim 1, wherein a radial stiffness of the distal segment is greater than a radial stiffness of the proximal segment.

5. The method of claim 1, wherein an inner diameter of the distal segment is greater than an inner diameter of the proximal segment.

6. The method of claim 1, wherein an area moment of inertia of the distal segment is greater than an area moment of inertia of the proximal segment.

7. The method of claim 1, wherein a construction of the distal segment differs from a construction of the proximal segment.

8. A method of repairing a defective heart valve of a patient, the method comprising:
   receiving a delivery system loaded with a radially self-expandable prosthetic heart valve having a stent frame to which a valve structure is attached, the delivery system including an inner shaft assembly coaxially received within a delivery sheath assembly having a capsule forming a distal segment and a proximal segment, the distal segment having an outer diameter greater than an outer diameter of the proximal segment, and an axial length of the distal segment is less than an axial length of the stent frame, wherein the distal segment is disposed over and compressively retains and contacts a distal region of the prosthetic heart valve and the proximal segment is disposed over and compressively retains and contacts a proximal region of the prosthetic heart valve such that the prosthetic heart valve is entirely compressibly retained within the capsule;
   inserting the prosthetic heart valve into a bodily lumen while the prosthetic heart valve is constrained within the capsule;
   manipulating the delivery system to guide the prosthetic heart valve through the patient's vasculature and into the defective heart valve; and
   withdrawing the capsule from the prosthetic heart valve to permit the prosthetic heart valve to self-expand and release from the delivery system and into engagement with the native heart valve.

9. The method of claim 8, wherein manipulating the delivery system to guide the prosthetic heart valve through the patient's vasculature includes tracking the prosthetic heart valve around the patient's aortic arch.

10. The method of claim 9, wherein tracking the prosthetic heart valve around the patient's aortic arch includes the capsule not experiencing kinking when tracking across the patient's aortic arch.

11. The method of claim 8, wherein prior to the step of withdrawing the capsule to permit the prosthetic heart valve to release from the delivery system, the method further comprising:
   partially retracting the capsule from the prosthetic heart valve such that an exposed region of the prosthetic heart valve self-expands while a trailing region of the prosthetic heart valve remains constrained within the capsule; and
   distally advancing the capsule over the exposed region to recapture the prosthetic heart valve relative to the delivery system.

* * * * *